United States Patent
Garst et al.

(10) Patent No.: US 9,561,259 B2
(45) Date of Patent: Feb. 7, 2017

(54) CYCLOSPORIN ANALOGS

(71) Applicant: Allergan, Inc., Irvine, CA (US)

(72) Inventors: Michael E. Garst, Newport Beach, CA (US); William Robert Carling, Bishops Stortford (GB); David Arthur Scowen, Essex (GB); Michael E. Stern, Mission Viejo, CA (US); Christopher S Schaumburg, Huntington Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/873,908

(22) Filed: Oct. 2, 2015

(65) Prior Publication Data

US 2016/0022765 A1    Jan. 28, 2016

Related U.S. Application Data

(62) Division of application No. 13/270,929, filed on Oct. 11, 2011, now Pat. No. 9,175,042.

(60) Provisional application No. 61/392,451, filed on Oct. 12, 2010.

(51) Int. Cl.
    *C07K 7/64* (2006.01)
    *A61K 38/13* (2006.01)

(52) U.S. Cl.
    CPC ............ *A61K 38/13* (2013.01); *C07K 7/645* (2013.01)

(58) Field of Classification Search
    CPC ................................................... C07K 7/645
    USPC ....................................................... 530/317
    See application file for complete search history.

(56) References Cited

U.S. PATENT DOCUMENTS

| | | | |
|---|---|---|---|
| 4,649,047 A | 3/1987 | Kaswan | |
| 5,474,979 A | 12/1995 | Ding et al. | |
| 5,965,527 A | 10/1999 | Barriere et al. | |
| 5,977,067 A | 11/1999 | Evers et al. | |
| 5,994,299 A | 11/1999 | Barriere et al. | |
| 6,583,265 B1 | 6/2003 | Ellmerer-Muller et al. | |
| 2010/0009953 A1 | 1/2010 | Garst | |
| 2012/0088734 A1 | 4/2012 | Frydrych et al. | |
| 2013/0210704 A1 | 8/2013 | Su et al. | |

FOREIGN PATENT DOCUMENTS

| | | |
|---|---|---|
| CN | 101687013 A | 3/2010 |
| JP | 2001524105 A | 11/2001 |
| JP | 2002518406 A | 6/2002 |
| WO | 9932512 A1 | 7/1999 |
| WO | 99-65933 A1 | 12/1999 |
| WO | 00-61168 A1 | 10/2000 |
| WO | 200061168 A1 | 10/2000 |
| WO | 2008-137617 A1 | 11/2008 |
| WO | 2010-006117 A2 | 1/2010 |
| WO | 2012-009715 A2 | 1/2012 |
| WO | 2012-021796 A2 | 2/2012 |
| WO | 2012-051194 A1 | 4/2012 |
| WO | 2012-075494 A1 | 6/2012 |

OTHER PUBLICATIONS

Australian Patent Application No 2011316689, Patent Examination Report 1, Sep. 30, 2014, pp. 4, Australian Government IP Australia.
Chinese Applicaiton No. 201180059696X, First Office Action, State Intellectual Property Office of the People's Republic of China, May 12, 2014, (including English translation) pp. 11.
European Patent Application No. 11770984.0, Communication Pursunat to Rules 161(1) and 162 EPC, May 23, 2013, pp. 2, European Patent Office.
U.S. Appl. No. 12/499,911, filed Jul. 9, 2009.
U.S. Appl. No. 13/270,964, filed Oct. 11, 2011.
U.S. Appl. No. 61/134,510, filed Jul. 10, 2008.
U.S. Appl. No. 61/392,449, filed Oct. 12, 2010.

*Primary Examiner* — David Lukton

(74) *Attorney, Agent, or Firm* — Barbara C. Potts

(57) ABSTRACT

Disclosed herein are novel analogs of cyclosporin, pharmaceutical compositions containing them, and methods for their use in the treatment of dry eye and other conditions.

5 Claims, No Drawings

CYCLOSPORIN ANALOGS

CROSS REFERENCE TO RELATED APPLICATIONS

This application is a divisional application of U.S. Non-Provisional patent application Ser. No. 13/270,929, filed on Oct. 11, 2011, which claims the benefit of U.S. Provisional Patent Application Ser. No. 61/392,451, filed on Oct. 12, 2010, the entire disclosure of each of which is incorporated herein by this specific reference.

Disclosed herein are novel analogs of cyclosporin, pharmaceutical compositions containing them, and methods for their use in the treatment of dry eye and other conditions.

BACKGROUND

Cyclosporins are a class of poly-N-methylated cyclic undecapeptides. There are naturally occurring cyclosporins ("Cs") such as Cs A, and non-natural cyclosporin derivatives.

Cyclosporin A, for example, has the following structure:

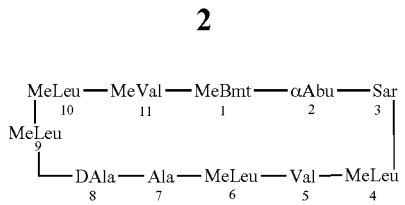

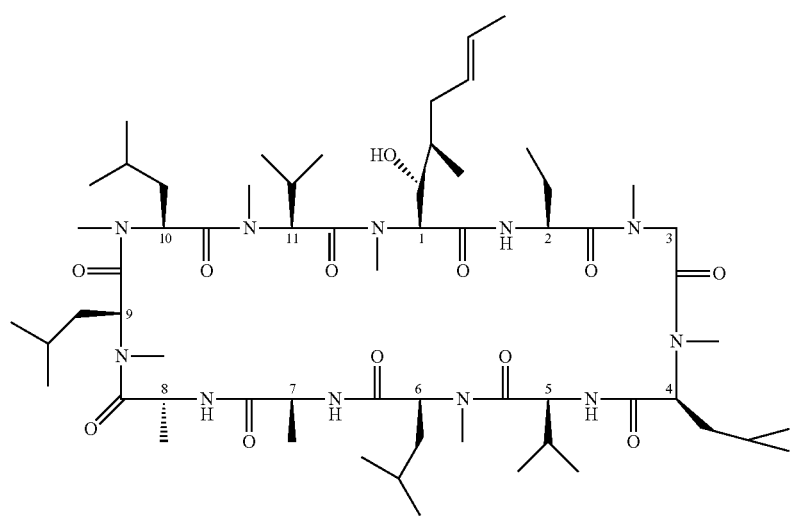 [SMILES: C/C=C/C[C@@H](C)[C@@H](O)[C@@H]1C(=O)N[C@H](CC)C(=O)N(C)CC(=O)N(C)[C@@H](CC(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N1C]

The following structure shows the 11 amino acid residues of cyclosporin A:

DETAILED DESCRIPTION

The claimed invention relates to novel compounds of the following formula (I) or pharmaceutically acceptable salts thereof:

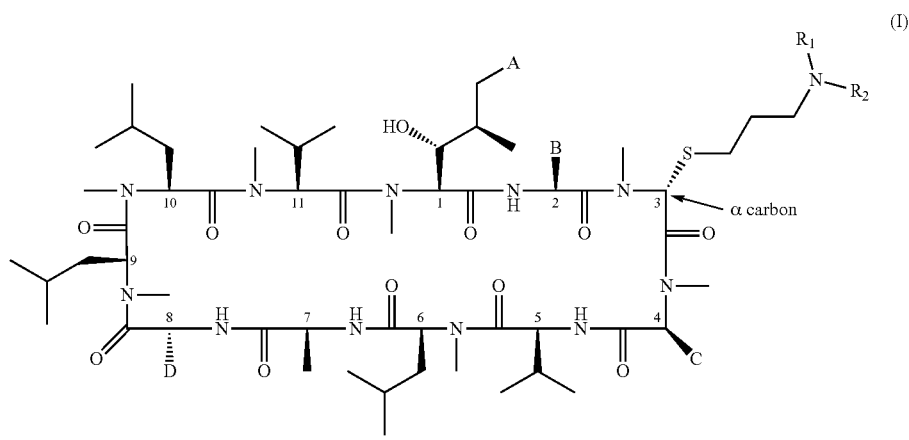

(I)

The claimed novel compounds of formula (I) result from modifications at the α-carbon of the 3-position amino acid (sarcosine) of "Cs scaffolds," which as used herein refers to different cyclosporins (e.g., Cs A, Cs C, Cs D, etc.) that vary from each other in the identities of one or more of substituents A, B, C, and D. In other words, a "Cs scaffold" refers to a novel compound of formula (I) less the moiety at the α-carbon of the 3-position amino acid.

A represents
(a) —CH=CHR,
(b) —CH=CH—CH=CHR,
or
(c) —CH$_2$CH$_2$R,
wherein R represents
(a) —CH$_3$,
(b) —CH$_2$SH,
(c) —CH$_2$S—C$_n$, wherein n=1-6,
(d) —CH$_2$-carboxyl

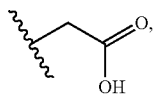 [SMILES: *CC(=O)O]

(e) carboxyl

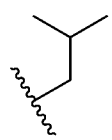 [SMILES: *CC(C)C]

(f) alkoxycarbonyl

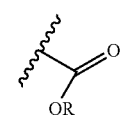

wherein R=C$_1$-C$_6$ alkyl,
or
(g) —CH$_2$-alkoxycarbonyl

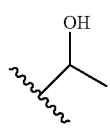

wherein R=C$_1$-C$_6$ alkyl;
B represents
(a) —CH$_2$CH$_3$,
(b) 1-hydroxyethyl, (c) isopropyl

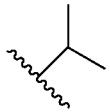

or
(d) n-propyl;

C represents
(a) isobutyl,

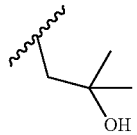 [SMILES: *CC(C)(C)O]

(b) 2-hydroxyisobutyl

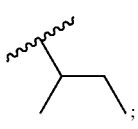 [SMILES: *C(C)CC]

or
(c) 1-methylpropyl

D represents
(a) —CH$_3$
or
(b) —CH$_2$OH.

In one embodiment of the present invention, A is —CH=CHCH$_3$, B is —CH$_2$CH$_3$, C is isobutyl, and D is —CH$_3$, as illustrated below in formula (IA):

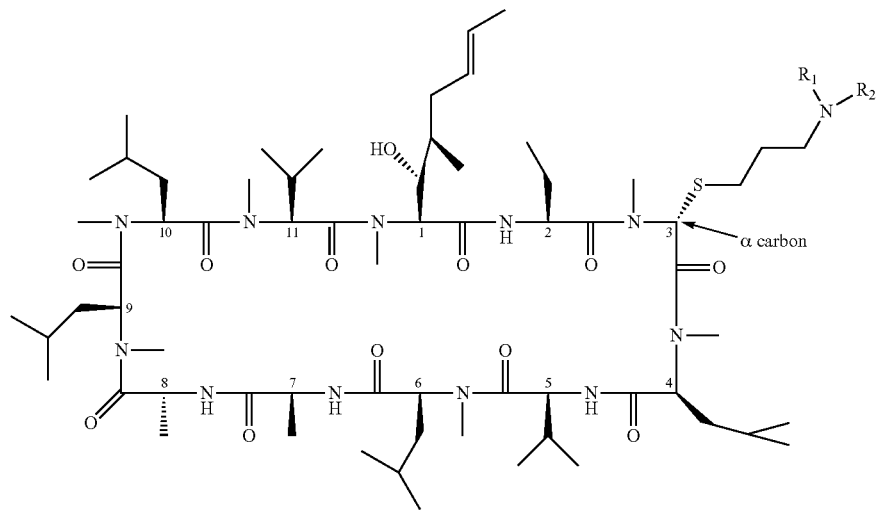
(IA)
In one embodiment, A is —CH=CHCH₃, B is 1-hydroxyethyl, C is isobutyl, and D is —CH₃, as illustrated below in formula (IB):
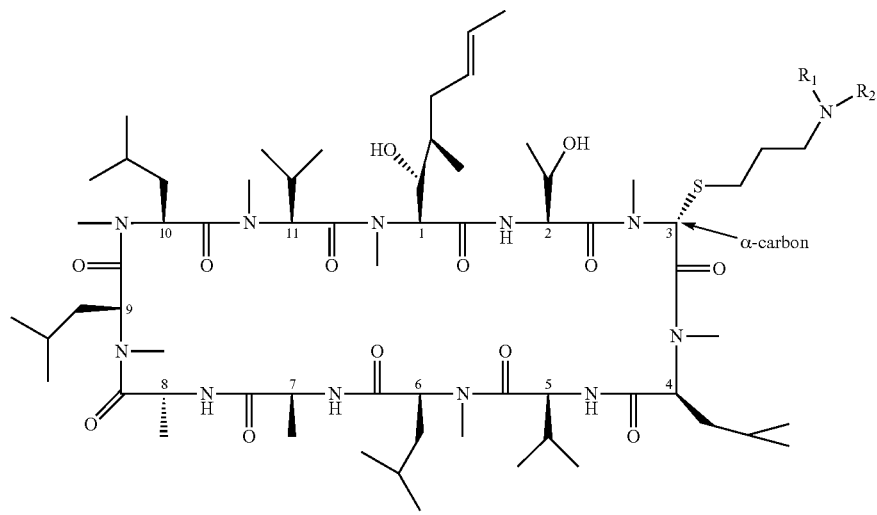
(IB)
In one embodiment, A is —CH=CHCH₃, B is isopropyl, C is isobutyl, and D is —CH₃, as illustrated below in formula (IC):

(IC)
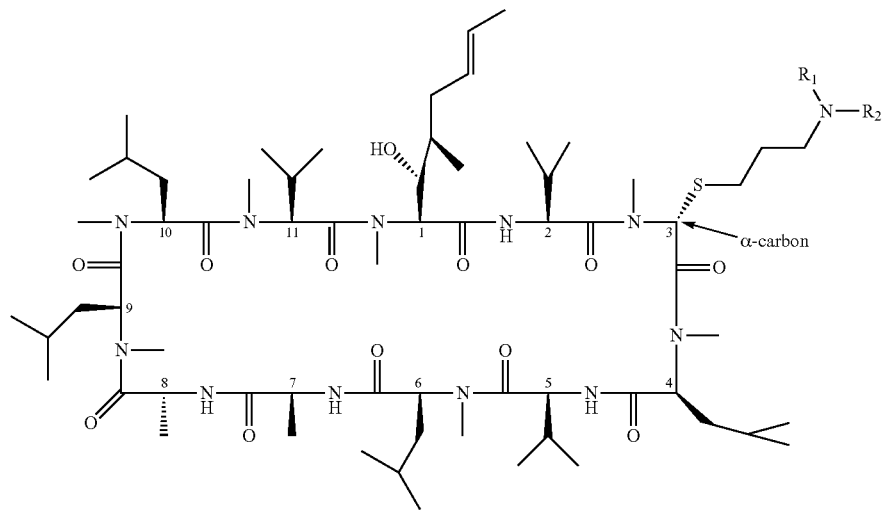
In one embodiment, A is —CH=CHCH₃, B is n-propyl, C is isobutyl, and D is —CH₃, as illustrated below in formula (ID):
(ID)
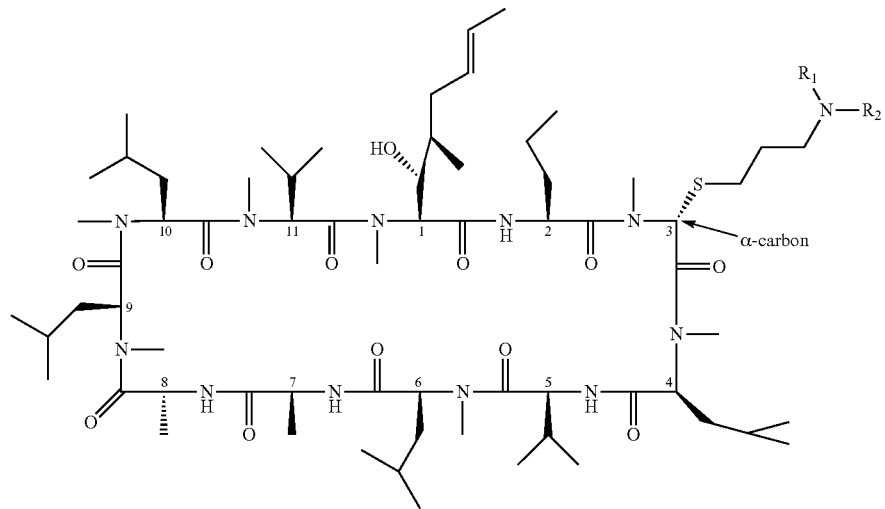
In one embodiment, A is —CH=CHCH₃, B is —CH₂CH₃, C is 1-methylpropyl, and D is —CH₃, as illustrated below in formula (IE):

In formula (I), the amino acids of various types of cyclosporin scaffold are labeled numerically from 1 to 11. The said modification occurs at the α-carbon of the position-3 amino acid (sarcosine at the 3-position) of the Cs scaffold. The modification generally comprises replacement of a hydrogen atom at the (IE)

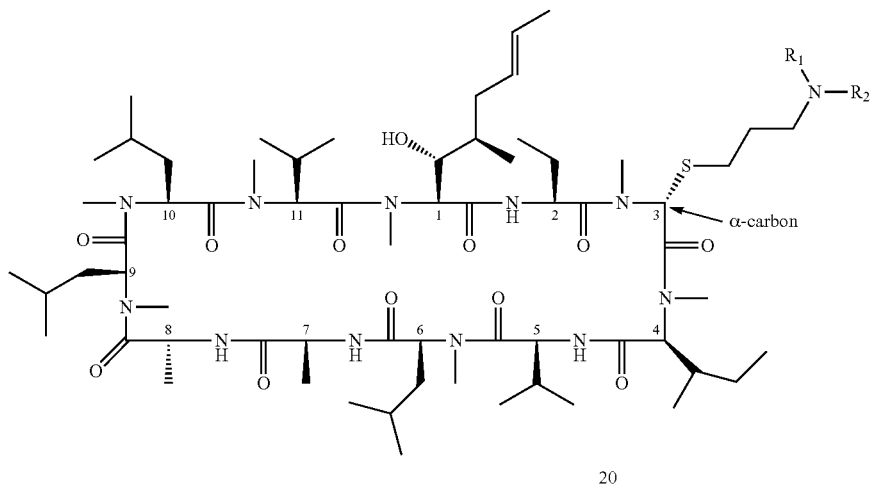

In one embodiment, A is —CH═CHCH₃, B is —CH₂CH₃, C is isobutyl, and D is —CH₂OH, as illustrated below in formula (IF):

(IF)

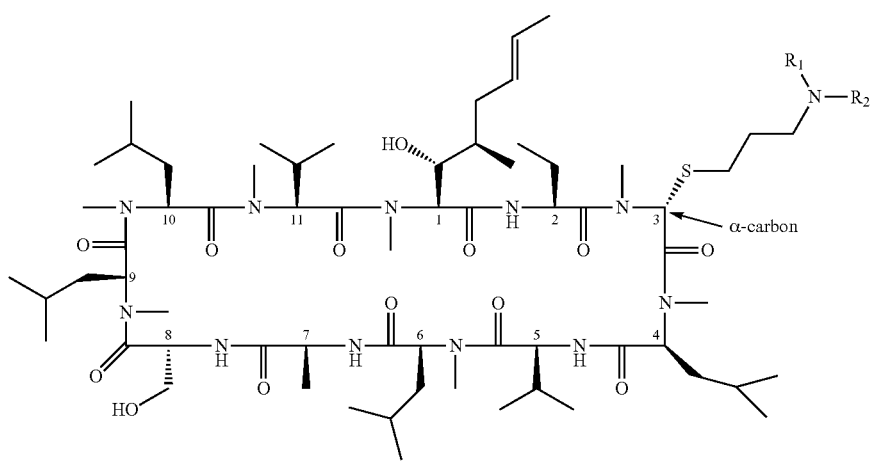

In one embodiment, A is —CH═CHCH₃, B is —CH₂CH₃, C is 2-hydroxy isobutyl, and D is —CH₃, as illustrated below in formula (IG):

(IG)

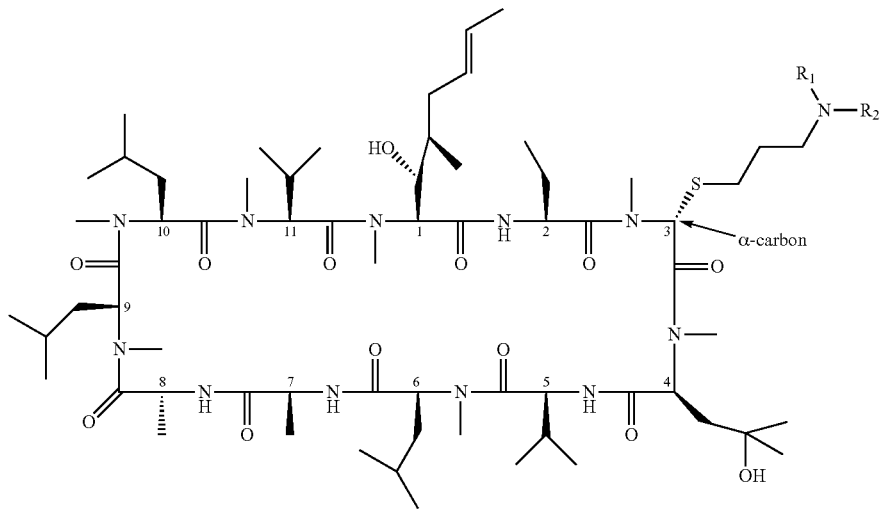

α-carbon of the position-3 amino acid with a moiety in formula (I) wherein:

$R_1$ and $R_2$, which are identical or different, independently represent
(a) $C_1$-$C_6$ alkyl
or
(b) mono, di, or trifluorinated alkyl,
(c) $R_1$ and $R_2$, together with the nitrogen atom to which they are attached, may form a saturated or partially unsaturated 3-7 member heterocycloalkyl containing one other heteroatom selected from oxygen;
S(O)n, wherein n=0, 1, 2;
and nitrogen which is optionally substituted with $C_1$-$C_6$ alkyl or fluoroalkyl.

COMPOUND EXAMPLES

Embodiments of formula (I) include, but are not limited to, the following compounds of formula (I) (only the moiety at the α-carbon of the position-3 amino acid is shown; wavy lines represent the rest of the Cs compounds of formula (I)):

Compound Example 1

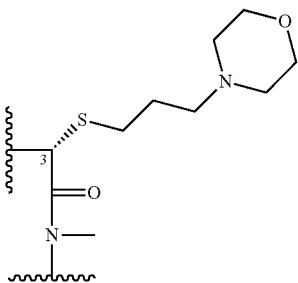 [SMILES: *[C@H](SCCCN1CCOCC1)C(=O)N(*)C]

Compound Example 2

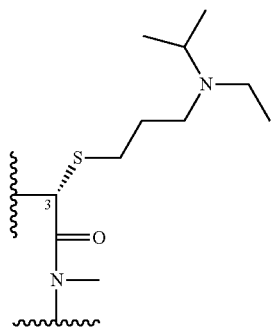 [SMILES: *[C@H](SCCCN(CC)C(C)C)C(=O)N(*)C]

Compound Example 3

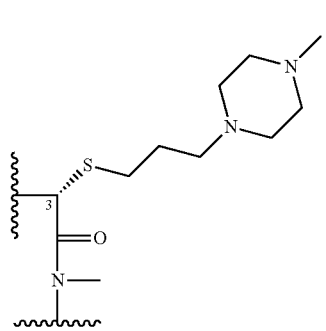 [SMILES: *[C@H](SCCCN1CCN(C)CC1)C(=O)N(*)C]

DEFINITIONS

"Alkyl" refers to a monovalent linear or branched hydrocarbon radical having 1 to 6 carbon atoms. Examples include, but are not limited to, methyl, ethyl, propyl (e.g., 1-propyl, isopropyl), butyl (e.g., 1-butyl, isobutyl, sec-butyl, tert-butyl), pentyl (e.g., 1-pentyl, neopentyl), and hexyl (e.g., 3-hexyl).

"Fluoroalkyl or fluorinated alkyl" refers to an alkyl, as defined herein, substituted by one or more groups of fluorine.

"Alkenyl" refers to a monovalent linear or branched hydrocarbon radical having 2 to 6 carbon atoms and one or more double bonds. Examples include, but are not limited to, ethenyl, propenyl, and butenyl.

"Alkynyl" refers to a monovalent linear or branched hydrocarbon radical having 2 to 6 carbon atoms and one or more triple bonds. Examples include, but are not limited to, ethynyl, propynyl and butynyl.

"Cycloalkyl" refers to monovalent saturated or partially unsaturated cyclic hydrocarbon radical having 3 to 6 carbon atoms. Examples include, but are not limited to, cyclopropyl, cyclobutyl, cyclopentyl, and cyclohexyl.

"Heterocyclyl" refers to monovalent, saturated or partially unsaturated cyclic hydrocarbon radical having 3 to 6 ring atoms, at least one of which is a heteroatom selected from nitrogen, oxygen and sulfur. The radical may be on a carbon or a heteroatom. Examples include, but are not limited to, morpholinyl, piperidinyl, pyrrolidinyl, pyranyl, and pyrazolinyl.

"Heteroaryl" refers to monovalent 5-7 member aromatic hydrocarbon radical having one or more heteroatoms selected from nitrogen, sulfur and oxygen. Examples include, but are not limited to, imidazolyl, pyridinyl, furyl, pyrimidinyl and pyrazinyl.

The aforementioned alkyl, cycloalkyl, and heterocyclyl radicals may be independently substituted with one or more substituents described herein.

"Amino" refers to the —$NH_2$ or amidogen group.

"Monoalkylamino" refers to the —NHR' group, where R' represents an alkyl as defined herein.

"Dialkylamino" refers to the —NRR' group where R and R' independently represents an alkyl as defined herein.

"Hydroxyl" refers to the —OH group.

"Carboxyl" refers to the group:

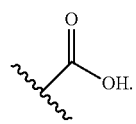

"Alkoxycarbonyl" refers to the group:

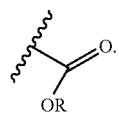

where R represents an alkyl as defined herein.

"Pharmaceutically acceptable salt" refers to any salt of compounds claimed in this application that possesses the biological effectiveness to the said compounds and are not toxic or otherwise harmful for pharmaceutical use; these salts may be derived from organic and inorganic counter ions which are well known in the art.

SYNTHESIS EXAMPLES

The invention is illustrated by the following non-limiting synthesis examples.

Unless otherwise indicated, the following chemical abbreviations are used in the synthesis examples:
Ac: acetone
DCM: dichloromethane
LDA: lithium diisopropylamide
Me: methyl
THF: tetrahydrofuran The Cs scaffold, the starting material for the claimed compounds of formula (I), can be prepared using synthesis schemes and reagents available in the art, and may be obtained through commercial suppliers. Reagents used for the synthesis of the novel compounds of the present invention can also be obtained through commercial suppliers.

Synthesis Example 1

[(R)-(3-morpholin-4-yl-propylthio)-Sar]$^3$ Cyclosporin A

Step 1: Synthesis of Toluene-4-thiosulfonic acid S-(3-chloropropyl) ester

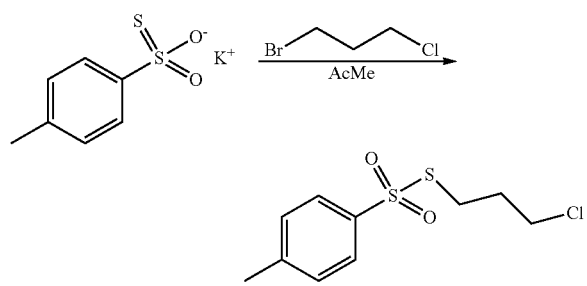

Potassium thiotosylate (50.0 g, 221 mmol, 1.0 eq.) and 1-bromo-3-chloropropane (38.0 g, 241 mmol, 1.09 eq.) were stirred together in acetone (1 L) at room temperature for 72 hours. The mixture was then concentrated. Next, the mixture was partitioned between dichloromethane and water. The organic solution was washed with brine (2×), dried using MgSO$_4$, concentrated and azeotroped with toluene to produce a pale yellow oil weighing 54 g (92%).

1H NMR (CDCl$_3$, ppm) δ 7.84 (d, J=8.4 Hz, 2H), 7.37 (d, J=8.2 Hz, 2H), 3.59 (t, J=6.1 Hz, 2H), 3.15 (t, J=7.0 Hz, 2H), 2.48 (s, 3H), 2.14 (m, J=7.0 Hz, 2H).

Step 2: Synthesis of Toluene-4-thiosulfonic acid S-(3-morpholin-4-yl-propyl)ester

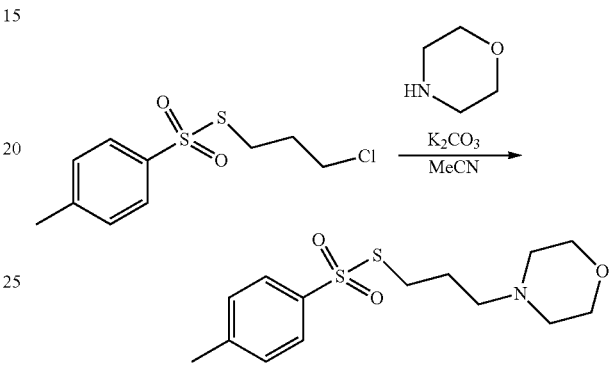

Toluene-4-thiosulfonic acid S-(3-chloro-propyl)ester (61.7 g, 233 mmol, 1.00 eq.), morpholine (22.2 g, 255 mmol, 1.09 eq.) and potassium carbonate (33.8 g, 240 mmol, 1.06 eq.) were stirred together in acetonitrile (1 L) for 64 hours at 50° C. The mixture was concentrated, then partitioned between ethyl acetate and water. The organic solution was washed with water (2×), dried using MgSO$_4$, and concentrated to produce a light yellow oil weighing 61.5 g (84%).

1H NMR (300 MHz, CDCl$_3$, ppm) δ 7.83 (d, J=8.4 Hz, 2H), 7.36 (d, J=8.2 Hz, 2H), 3.68 (t, J=4.8 Hz, 4H), 3.07 (t, J=7.0 Hz, 2H), 2.47 (s, 3H), 2.39-2.33 (m, 6H), 1.84 (m, 6.7 Hz, 2H).

Step 3: Synthesis of [(R)-(3-Morpholin-4-yl-propylthio)-Sar]$^3$ Cyclosporin A

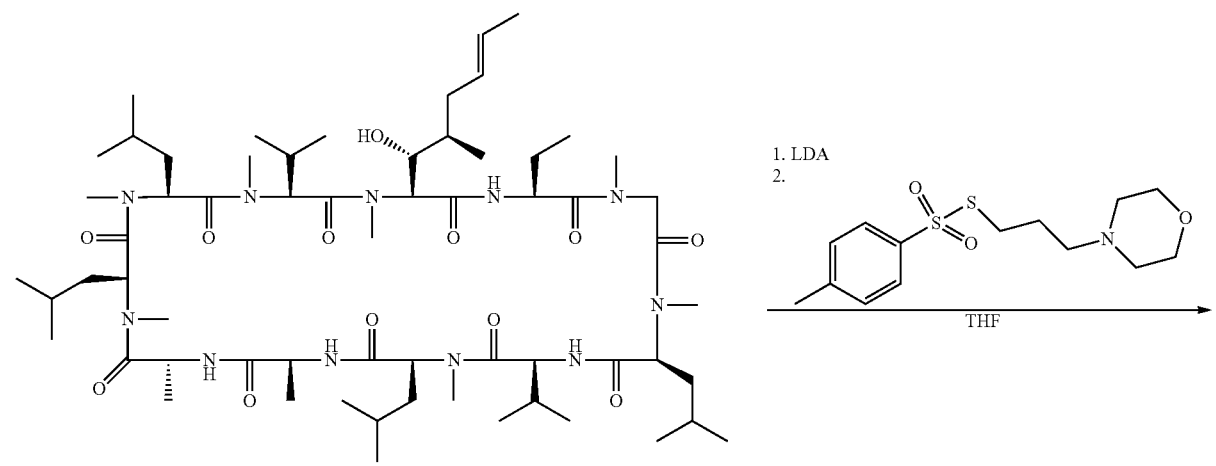

Cyclosporin A

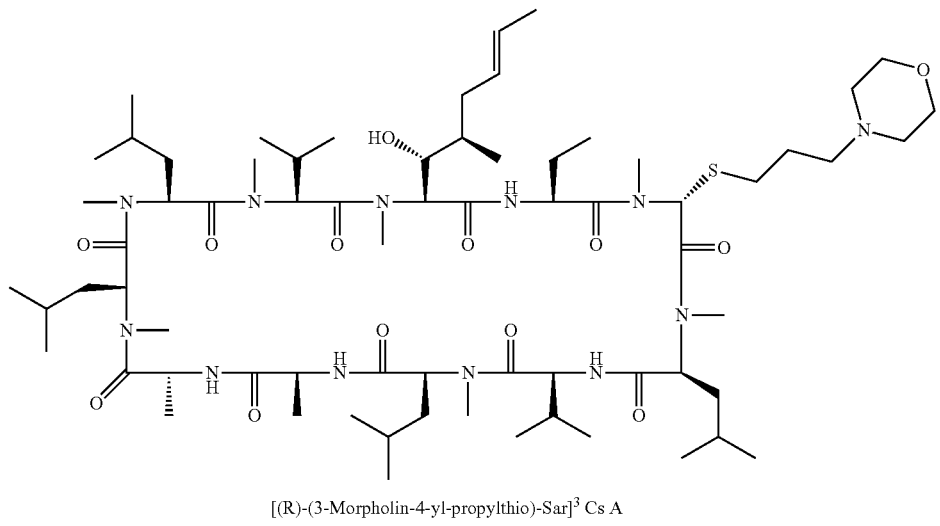

[(R)-(3-Morpholin-4-yl-propylthio)-Sar]³ Cs A

First, diisopropylamine (13.3 ml, 95 mmol, 10 eq.) was added to a solution of n-butyllithium (2.5 M in hexanes, 38 ml, 95 mmol, 10 eq.) in THF (238 ml) at −78° C. under an atmosphere of nitrogen; the resulting mixture was stirred for 90 minutes. Next, a solution of cyclosporine A (11.4 g, 9.5 mmol, 1.0 eq.; azeotropically dried immediately prior to use with toluene) in THF (38 ml) was added to the mixture, which was then stirred under the same conditions (−78° C. under an atmosphere of nitrogen) for 2.5 hours. Then, toluene-4-thiosulfonic acid S-(3-morpholin-4-yl-propyl)ester (13.5 g, 42.8 mmol, 4.5 eq.) in THF (5 ml) was added; the resulting mixture was allowed to warm to room temperature while being stirred for 2 hours. Subsequently, the mixture was cooled to −20° C. and acetic acid (6.0 ml, 105 mmol, 11 eq.) was added. The mixture was allowed to warm to room temperature overnight. After the solvent was evaporated from the mixture, the resultant mixture was partitioned between ethyl acetate and saturated ammonium chloride solution. The organic phase was washed first with ammonium chloride solution, then brine; dried using MgSO₄, and concentrated. The crude product was purified by MPLC (SiO₂, diethyl ether then 5% methanol/95% diethyl ether then 5% (10% aqueous ammonia/90% methanol)/95% diethyl ether. The material obtained was further purified by HPLC (SiO2, 4.5% MeOH/95.5% dichloromethane) to afford 800 mg (6%) of a white amorphous solid.

ESMS MH⁺1361.9.

1H NMR (CDCl3, ppm, diagnostic protons) δ 7.95 (d, J=10 Hz, 1H, amide NH), 7.69 (d, J=8 Hz, 1H, amide NH), 7.35 (d, J=8 Hz, 1H, amide NH), 7.17 (d, J=8 Hz, 1H, amide NH), 5.97 (s, 1H, sarcosine H).

Synthesis Example 2

[(R)-(3-ethylisopropylamino-propylthio)-Sar]³ Cyclosporin A

Step 1: Synthesis of Toluene-4-thiosulfonic acid S-[3(ethylisopropylamino)-propyl]ester

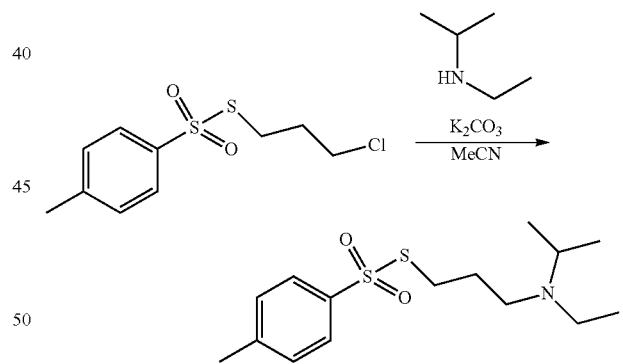

Toluene-4-thiosulfonic acid S-(3-chloro-propyl)ester (12.0 g, 45.3 mol, 1.00 eq.), N-ethylisopropylamine (4.2 g, 48.0 mmol, 1.05 eq.) and potassium carbonate (6.9 g, 49.9 mmol, 1.10 eq.) were stirred together in acetonitrile (160 mL) at 60° C. for 18 hours. The mixture was concentrated in vacuo and the residue was partitioned between ethyl acetate (500 mL) and water (250 mL). The organic solution was washed with brine (250 mL), dried (MgSO4) and the resulting oil was purified by MPLC chromatography to give an oil weighing 2.98 g (21%).

1H NMR (CDCl3, ppm) δ 7.83 (d, J=8 Hz, 2H), 7.35 (d, J=8 Hz, 2H), 3.08 (t, J=7 Hz, 2H), 2.88 (m, J=7 Hz, 1H), 2.48 (s, 3H), 2.39 (m, 4H), 1.75 (m, J=7 Hz, 2H), 0.95 (t, 7 Hz, 2H), 0.90 (d, 7 Hz, 6H).

Step 2:
[(R)-(3-ethylisopropylamino-propylthio)-Sar]³ Cyclosporin A

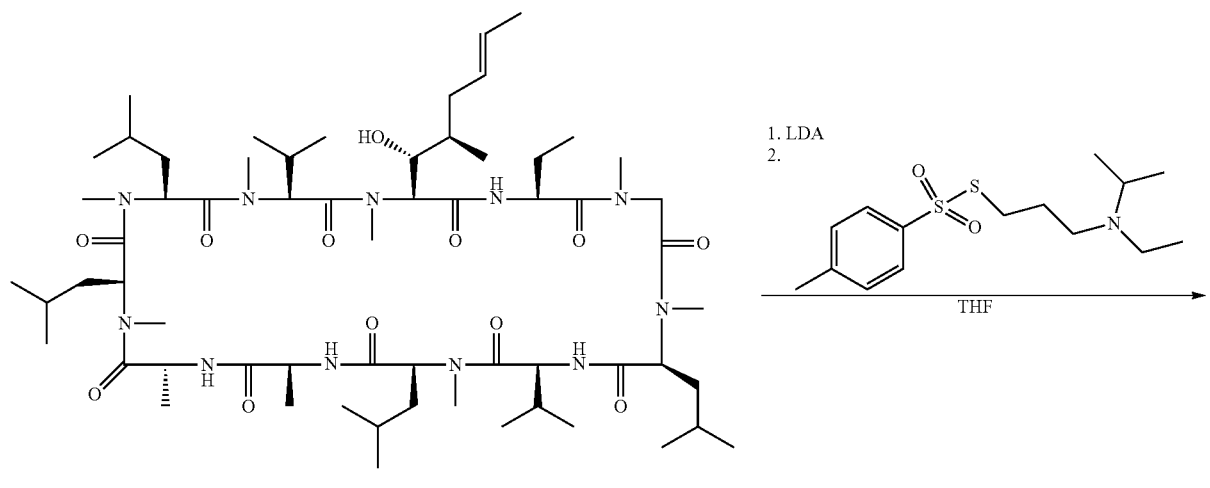

Cyclosporin A

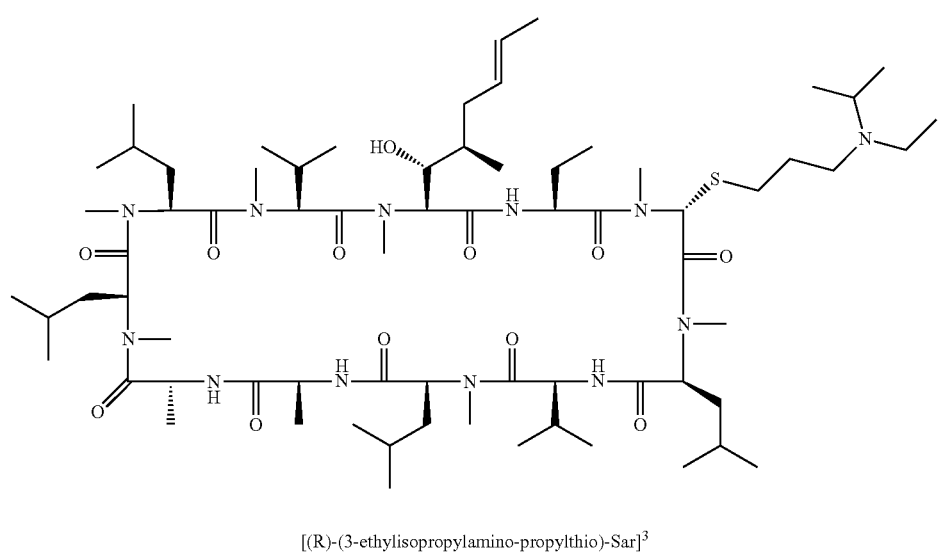

[(R)-(3-ethylisopropylamino-propylthio)-Sar]³ cyclosporin A

First, n-Butyllithium (1.6M in hexanes, 17.5 ml, 28 mmol, 10 eq.) was added dropwise (under an atmosphere of nitrogen) to a solution of diisopropylamine (3.92 ml, 28 mmol, 10 eq.) in THF (70 ml) at 0° C. The mixture was stirred at −10° C. for 30 minutes and cooled to −78° C. under an atmosphere of nitrogen.

Next, a solution of cyclosporin A (3.35 g, 2.8 mmol, 1.0 eq.; azeotropically dried immediately prior to use with toluene) in THF (10 ml) was added and the reaction mixture was stirred under the same conditions for 2.5 hours. Toluene-4-thiosulfonic acid S-[3-(ethylisopropylamino)-propyl] ester (4.4 g, 13.9 mmol, 5.0 eq.) in THF (10 ml) was then added and the resulting mixture was allowed to warm to room temperature and stirred for 1 hour. The mixture was cooled to −78° C. before acetic acid (1.8 ml, 31 mmol, 11 eq.) was added to it; the mixture was allowed to warm to room temperature overnight. The solvent was evaporated and the resultant mixture was partitioned between ethyl acetate (600 mL) and saturated ammonium chloride solution (300 ml). The organic phase was first washed with ammonium chloride solution (2×200 ml), then water (200 ml); dried using $MgSO_4$, and concentrated in vacuo to give a thick oil.

The crude product was purified by MPLC ($SiO_2$, ethyl acetate, then 10% methanol/90% ethyl acetate, then 10% (7M ammonia in methanol)/90% ethyl acetate), by trituration with hexane (removal of excess reagent), by use of SCX column (removal of remaining CsA), and finally HPLC ($SiO_2$, 4.5% MeOH/95.5% dichloromethane) to afford 385 mg (10%) of a white amorphous solid.

ESMS $MH^+$ 1362.1.

1H NMR (500 MHz, CDCl3, ppm, diagnostic protons) δ 7.95 (d, J=10 Hz, 1H, amide NH), 7.68 (d, J=8 Hz, 1H, amide NH), 7.32 (d, J=8 Hz, 1H, amide NH), 7.18 (d, J=8 Hz, 1H, amide NH), 5.87 (s, 1H, sarcosine H).

Synthesis Example 3

[(R)-(3-(4-methyl-piperazin-1-yl)-propylthio)-Sar]³ Cyclosporin A

Step 1: Synthesis of Toluene-4-thiosulfonic acid S-[3-(4-methyl-piperazin-1-yl)-propyl]ester

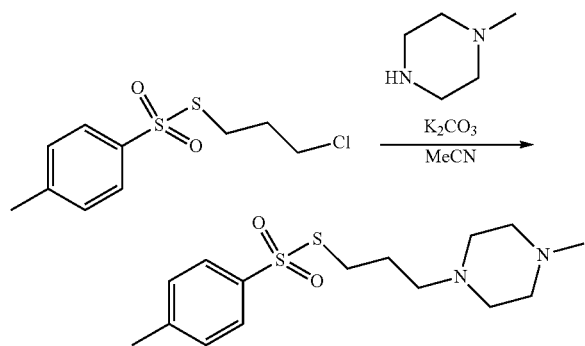

Toluene-4-thiosulfonic acid S-(3-chloro-propyl)ester (4.9 g, 18.4 mol, 1.00 eq.), N-methylpiperazine (1.9 g, 19.3 mmol, 1.05 eq.) and potassium carbonate (2.7 g, 19.4 mmol, 1.05 eq.) were stirred together in acetonitrile (100 mL) at room temperature for 64 hours. The mixture was concentrated and the residue was partitioned between ethyl acetate (500 ml) and water (250 ml). The organic solution was washed with water (2×200 mL), dried using $MgSO_4$, concentrated and purified by MPLC to give a light yellow oil weighing 2.1 g (36%).

1H NMR ($CDCl_3$, ppm) δ 7.83 (d, J=8 Hz, 2H), 7.35 (d, J=8 Hz, 2H), 3.05 (t, J=7 Hz, 2H), 2.47 (s, 3H), 2.41 (broad, 4H), 2.35 (t, J=7 Hz, 2H), 2.29 (s, 3H), 2.47 (s, 3H), 2.39-2.33 (m, 6H), 1.82 (m, 7 Hz, 2H).

Step 2: Synthesis of [(R)-(3-(4-methyl-piperazin-1-yl)-propylthio)-Sar]³ Cyclosporin A

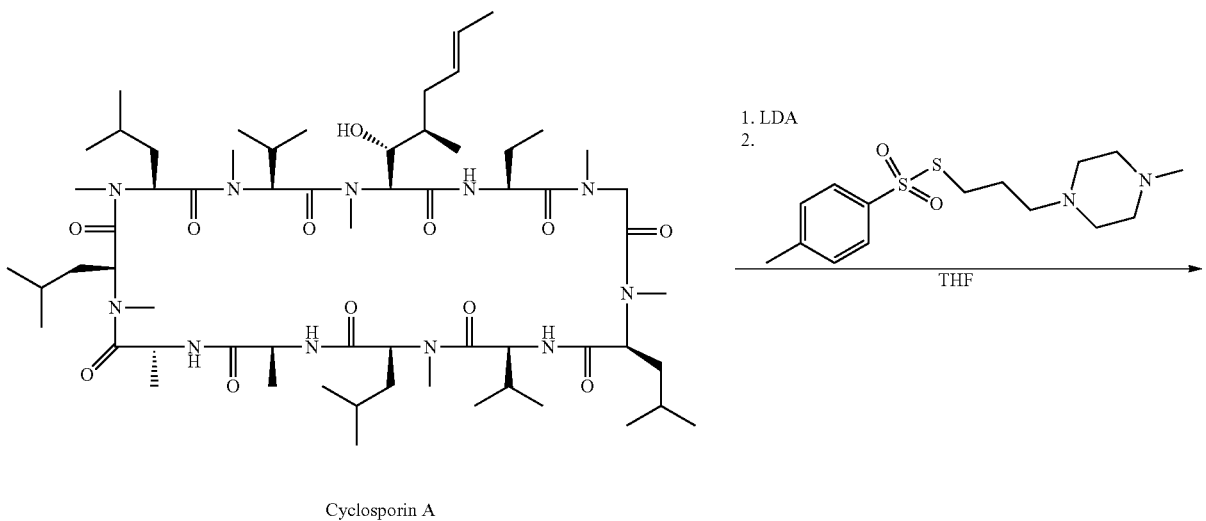

Cyclosporin A

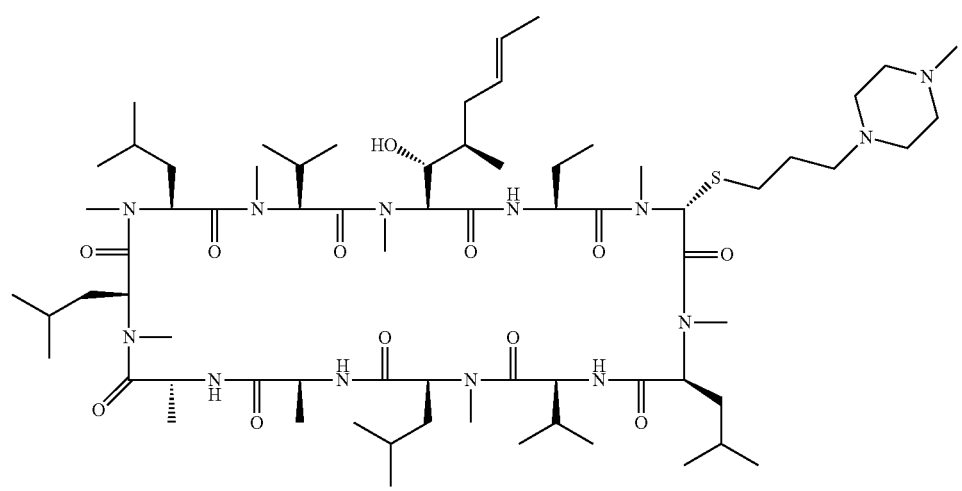

[(R)-(3-(4-Methyl-piperazin-1-yl)-propylthio)-Sar]³ Cyclosporin A

First, n-butyllithium (2.5M in hexanes, 10.5 ml, 26 mmol, 10 eq.) was added dropwise (under an atmosphere of nitrogen) to a solution of diisopropylamine (3.7 ml, 26 mmol, 10 eq.) in THF (70 ml) at −78° C. The mixture was stirred for 1 hour under these same conditions.

A solution of cyclosporin A (3.2 g, 2.6 mmol, 1.0 eq.; azeotropically dried immediately prior to use with toluene) in THF (15 ml) was added to the mixture and the mixture was stirred under the same conditions for 2 hours. Toluene-4-thiosulfonic acid S-[3-(4-methyl-piperazin-1-yl)-propyl] ester (4.3 g, 13 mmol, 5 eq.) in THF (15 ml) was then added and the resulting mixture was allowed to warm to room temperature and stirred for 90 minutes. The mixture was cooled to −70° C. before acetic acid (1.66 ml, 30 mmol, 11 eq.) was added. The mixture was allowed to warm to room temperature overnight. Next, the solvent was evaporated from the mixture and the resultant mixture was partitioned between ethyl acetate (500 mL) and saturated ammonium chloride solution (250 mL). The organic phase was washed first with ammonium chloride solution (200 mL), then brine (200 mL), dried using $MgSO_4$ and concentrated in vacuo.

The crude product was purified by MPLC (SiO2, diethyl ether, then 10% methanol/90% diethyl ether, then 10% (10% aqueous ammonia/90% methanol)/90% diethyl ether), by trituration with hexane (removal of excess reagent), by use of SCX column (removal of remaining CsA) and finally HPLC (SiO2, 6% MeOH/94% dichloromethane) to afford a white amorphous solid.

ESMS $MH^+$ 1374.89.

1H NMR (500 MHz, CDCl3, ppm, diagnostic protons) δ 7.92 (d, J=10 Hz, 1H, amide NH), 7.67 (d, J=8 Hz, 1H, amide NH), 7.30 (d, J=8 Hz, 1H, amide NH), 7.18 (d, J=8 Hz, 1H, amide NH), 5.86 (s, 1H, sarcosine H).

Test Data

Stability Data

Compounds of formula (I) exhibit the advantage of remaining stable in methanolic solutions. This indicates that formulations containing compounds of formula (I) would have a desirable shelf life, which is important for ocular medications since such medications are usually formulated as solutions, gels and the like. To demonstrate the stability of Examples 1-3 of the compounds of the current invention, their epimerization-in-MeOH data are contrasted with that of [(R)-(3-diethylaminoethylthio-Sar]$^3$ cyclosporin A in Table 1 below.

TABLE 1

Epimerization in MeOH at 50° C.

| Compound | Structure | Time (days) | Epimerization (%) |
|---|---|---|---|
| Example 1 [(R)-(3-morpholin-4-yl-propylthio)-Sar]$^3$ Cyclosporin A | 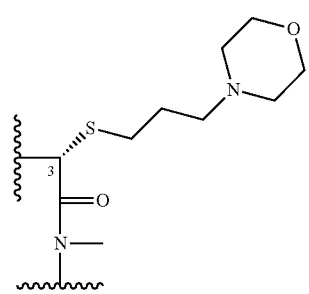 [SMILES: *[C@H](SCCCN1CCOCC1)C(=O)N(*)C] | 0<br>6<br>30 | 0<br>0<br>0.2 |
| Example 2 [(R)-(3-ethylisopropylamino-propylthio)-Sar]$^3$ Cyclosporin A | 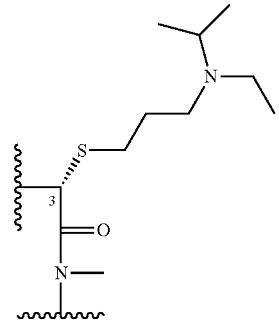 [SMILES: *[C@H](SCCCN(CC)C(C)C)C(=O)N(*)C] | 0<br>35 | 0<br>0 |

TABLE 1-continued

Epimerization in MeOH at 50° C.

| Compound | Structure | Time (days) | Epimerization (%) |
|---|---|---|---|
| Example 3 [(R)-(3-(4-methyl-piperazin-1-yl)-propylthio)-Sar]³ Cyclosporin A | | 0<br>30 | 0<br>2 |
| [(R)-(3-diethylaminoethylthio-Sar]³ cyclosporin A (not a compound of the current invention, used only for comparison) | | 0<br>1 | 0<br>15 |

Even though [(R)-(3-diethylaminoethylthio-Sar]³ cyclosporin A has similar biological activity (see table 2 below) as Examples 1-3 of the current invention, the data presented here show that the compounds of Examples 1-3 are significantly more stable in solution. It was discovered that [(R)-(3-diethylaminoethylthio)-Sar]³ cyclosporin A is unstable in both aqueous and methanolic solution and rapidly epimerizes to give a mixture of R- and S-isomers. In methanolic solution, the equilibrium ratio is ~4:1 R/S. The analysis of the relative rates of epimerization was carried out by comparison of 500 MHz nmr spectra. The proton attached to the sarcosine center (adjacent to the sulfur atom) appears at ~δ 5.9 in the R-isomer whilst in the S-isomer it moves downfield to ~δ6.5.

TABLE 2

Data Showing Cyp A Inhibitory Activity & Immunosuppressive Potential and Solution Stability of Compounds of Formula (I)

| Compound Example | *Reduction in rate of epimerization (relative to [(R)-(3-diethylaminoethylthio-Sar]³ cyclosporin A) at position 3 (α-carbon of the 3-position amino acid (sarcosine) of Cs scaffolds) | **Cyp A IC-50 (nM) Protease Free-PPIase Assay | ***CaN + Cyp A IC-50 (nM) | ****CaN − Cyp A IC50 (nM) | ****MLR IC50 (nM) |
|---|---|---|---|---|---|
| 1. | >1,000 | 1.7 | 4,200 | 3,900 | 3,000 |

TABLE 2-continued

Data Showing Cyp A Inhibitory Activity & Immunosuppressive Potential and Solution Stability of Compounds of Formula (I)

| Compound Example | *Reduction in rate of epimerization (relative to [(R)-(3-diethylaminoethylthio-Sar]$^3$ cyclosporin A) at position 3 (α-carbon of the 3-position amino acid (sarcosine) of Cs scaffolds) | **Cyp A IC-50 (nM) Protease Free-PPlase Assay | ***CaN + Cyp A IC-50 (nM) | ****CaN − Cyp A IC50 (nM) | ****MLR IC50 (nM) |
|---|---|---|---|---|---|
| 2. | >1,000 | 4.9 | 5,700 | 7,800 | 2,800 |
| 3. | >1,000 | 2.8 | 3,900 | 8,600 | 3,300 |
| [(R)-(3-diethylaminoethylthio-Sar]$^3$ cyclosporin A | 1 | 2.9 | 4,700 | 5,400 | 2,700 |

General Procedures Followed in Obtaining Data:
*carried out in methanol at 50° C. Conversion measured by 500 MHz NMR.
**Protease-free PPlase Assay The protease-free PPIase assay measures the rate of cis to trans conversion of a peptide substrate catalyzed by the enzyme cyclophilin A. Addition of an inhibitor slows the catalyzed rate and a $K_i$ value is obtained.

Materials
Assay Buffer:
 35 mM HEPES pH 7.8, filtered through a 0.2 µm filter. 50 µM DTT was added prior to use each day and then the buffer was stored on ice.

Enzyme:
 human recombinant Cyp A (Sigma C3805) enzyme was diluted to 1 µM with enzyme dilution buffer (20 mM HEPES pH 7.8, 40% glycerol, 50 µM DTT and 1 µM BSA) and stored at −20° C.

Substrate:
 SUC-AAPF-pNA (from Bachem AG, L-1400), 20 mg/ml prepared 0.5 M LiCl in trifluoroethanol.

Method
 All readings were taken with an Agilent 8453 Spectrophotometer which consists of a cuvette holder, stirrer and chiller to maintain a stirred cuvette temperature of 10.0±0.1° C. The temperature is monitored by the use of temperature probe. To prevent UV degradation of test compounds, the light below 290 nm was blocked using a glass slide in the light path. 1.5 ml of assay buffer was put into a 3 ml quartz cuvette and cooled to 10.0±0.1° C. while stirring (vigorous but not so fast as to produce cavitation). The inhibitor was diluted in 100% DMSO, and then added to the assay to a maximum final concentration of 0.5% DMSO in the assay. A blank spectrum was obtained, then 3 µL of enzyme was added (2 nM final concentration) and then 3 µL substrate (60 µM final concentration) added. The absorbance was measured at 330 nm for 300 s or 500 s for blank runs (NOTE: the substrate must be added in one quick injection and the measurements started immediately to minimize mixing errors).

A first order rate equation was fitted to the absorbance data, for each concentration of inhibitor, to obtain the rate constant (the first 10 to 15 seconds were excluded as mixing causes errors in this portion of curve). The catalytic rate was calculated from the enzymatic rate constant minus the background rate constant. An exponential curve was generated using the catalytic rate constants versus the inhibitor concentration to obtain the $K_i$ value for the inhibitor.

Calcineurin Phosphatase (CaN) Assay

Calcineurin is a serine-threonine protein phosphatase that on activation dephosphorylates members of the nuclear factor of activated T cells (NFAT), which are important in T lymphocyte activation. Cs A bound to cyclophilin A ("Cyp A") inhibits calcineurin activity, thus resulting in immunosuppressive effects. Although Cs A only inhibits calcineurin when bound to Cyp A, some Cs A analogues will also bind calcineurin in the absence of Cyp A. To investigate the immunosuppressive potential of exemplary compounds of Formula (I), which are cyclosporin analogues, their ability to inhibit calcineurin activity was measured in the presence and absence of Cyp A.

The CaN assay kit used is based on a colorimetric assay for measuring calcineurin phosphatase activity, and it is commercially available (Enzo Life Sciences and Calbiochem). Calmodulin is also required for calcineurin activity and RII phosphopeptide is used as an efficient peptide substrate for calcineurin. We have modified the method to enable measurement of Cyp A-dependent and Cyp-A-independent inhibition of calcineurin through the addition of Cyp A in a 1:1 complex with the inhibitor. The detection of free phosphate released is based on the classic Malachite green assay.

Materials Used
Enzo Life Sciences CaN Assay Kit: BML-AK804
2× Assay Buffer:
 100 mM Tris, pH 7.5, 200 mM NaCl, 12 mM $MgCl_2$, 1 mM DTT, 0.05% NP-40, 1 mM $CaCl_2$) $CaCl_2$).

Malachite Green:
 BIOMOL Green™ reagent

Calmodulin (Human, Recombinant):
 was thawed on ice, diluted 1:50 with 2× assay buffer, and then stored on ice.

Calcineurin:
 was thawed quickly, stored on ice immediately, diluted 1:12.5 with 1× assay buffer, and then stored on ice.

R-II Substrate:
 915 µL ultrapure water (UPW) was added to the 1.5 mg vial substrate to give a final concentration of 0.75 mM.

Inhibitors:
 2.5 mM inhibitor in 100% DMSO.

Cyp A:
 recombinant human Cyp A (Sigma C3805), 1 mg/ml.

Method
Inhibitor Dilutions:
 inhibitor compounds were diluted in UPW in polypropylene low-binding 96 well plates at 5× the final assay concentration. For samples 'without Cyp A', a 4-point dilution series of the inhibitor was prepared in duplicate to obtain a final assay concentration of 10, 1, 0.1 and 0.01 µM. For samples 'with Cyp A', a 7-point dilution series was prepared to obtain a 1:1 complex of the inhibitor with Cyp A; the inhibitor and Cyp A final assay concentrations of 10, 3.33, 1.11, 0.37, 0.12, 0.04, 0.014 µM were prepared. Cs A inhibitor controls were also prepared to obtain a final concentration of 10 µM Cs A with and without 10 µM Cyp A.

Assay Setup:
 using the half area 96 well plates supplied with the kit, 10 µl UPW was added to duplicate wells to provide the non-inhibited control. 10 µl of the inhibitor or the inhibitor/Cyp A complex was added to the appropriate sample wells. 25 µl of the 2× assay buffer with CaM was added to all wells, then 5 µl of CaN was added to all wells (40 U per well final concentration) except duplicate 'no calcineurin blank' wells to which 5 µL 1× assay buffer was added. The assay plate was placed in an oven at 30° C. for 15 minutes to equilibrate to the reaction temperature. The reaction was started by the addition of 10 µl RH-peptide (0.15 mM final concentration). The reaction was allowed to proceed at 30° C. for a time period in which the reaction is linear for about 60 minutes. The reaction was then terminated by adding 100 µl of the Malachite Green reagent. The color was allowed to develop for 15-30 minutes at room temperature before the absorbance at 620 nm was measured using a plate reader (Molecular Devices—SpectraMax M5). The data were analyzed by subtracting 'no Calcineurin blank' from all the absorbance readings and plotting the background corrected absorbances against $Log_{10}$ inhibitor concentration. A sigmoidal-dose response curve was fitted to the data using GraphPad Prism Software.

Mixed Lymphocyte Reaction ("MLR") Assay

The MLR assay is another means of estimating the immunosuppressive potential of test compounds. Female C57BL/6 and BALB/c mice, 6-8 weeks of age, were obtained from the Frederick Cancer Research and Development Center of the National Cancer Institute (Frederick, Md.). Spleens were harvested aseptically from all mice and single cell suspensions were prepared by disaggregating the cells with frosted glass slides, allowing the debris to settle, and washing the cells twice with complete medium. Complete medium consisted of RPMI 1640 medium containing 25 mM HEPES buffer (HyClone, Logan, Utah) supplemented with 10% heat-inactivated fetal bovine serum (FBS; Atlanta Biologicals, Lawrenceville, Ga.), 100 µg/mL streptomycin, 100 U/mL penicillin G, 0.25 µg/mL amphotericin B (HyClone), 2 mM L-glutamine dipeptide (HyClone), and $2\times10^{-5}$ M 2-mercaptoethanol (Sigma). Cells were washed twice and resuspended in complete medium. Cell counts were performed using a Beckman Coulter Z-1 particle counter (Fullerton, Calif.). Cell viability was determined by propidium iodide (PI) staining using an Accuri C6 flow cytometer (Ann Arbor, Mich.).

Spleen cells from C57BL/6 ($H-2^b$) and BALB/c ($H-2^d$) were used as responder (R) and stimulator (S) cells, respectively. Cells were plated in triplicate in 96-well flat microtiter plates (Costar, Cambridge, Mass.) such that each well contained $2\times10^5$ R and $8\times10^5$ S cells. Cultures were incubated in the absence or presence of various concentrations of Cs A, test compounds, or medium at 37° C. in humidified 5% $CO_2$ for five days, pulsed with $^3$H-thymidine ($^3$H-TdR) for the final 16 hours of incubation, and harvested using a Brandel 96-well cell harvester (Gaithersburg, Md.). Proliferation was measured by counting the radioactivity on filter mats in a Wallac 1450 Microbeta TriLux scintillation counter (Turku, Finland). Controls to demonstrate effective inactivation by the x-irradiation were performed by incubating the S cells with 5 µg/mL of PHA at $2\times10^5$ cells/well. These control cultures were incubated for 3 days under the same conditions as those described for the MLR; lymphoproliferation was determined in the same manner as described above.

Methods of Treatment

Compositions of the invention may be used to treat patients suffering from dry eye, to treat blepharitis and meibomian gland disease, to restore corneal sensitivity that has been impaired due to surgery on the cornea or other surface of the eye, to treat allergic conjunctivitis and atopic and vernal keratoconjunctivitis, and to treat pterygium, ocular symptoms of graft versus host disease, ocular allergy, atopic keratoconjunctivitis, vernal keratoconjunctivitis, uveitis, anterior uveitis, Behcet's disease, Steven Johnson syndrome, ocular cicatricial pemphigoid, chronic ocular surface inflammation caused by viral infection, herpes simplex keratitis, ocular rosacea, pinguecula, and to prevent corneal transplant rejection.

The International Dry Eye Workshop (DEWS) defines dry eye as "a multifactorial disease of the tears and ocular surface that results in symptoms of discomfort, visual disturbance, and tear film instability with potential damage to the ocular surface, accompanied by increased osmolarity of the tear film and inflammation of the ocular surface." It includes those conditions, such as keratoconjunctivitis sicca, that are caused by tear deficiency or excessive evaporation of tears.

Blepharitis is a chronic disorder producing inflammation of the anterior and posterior lid margin, with involvement of skin and its related structures (hairs and sebaceous glands), the mucocutaneous junction, and the meibomian glands. It can also affect the conjunctiva, tear film, and the corneal surface in advanced stages and may be associated with dry eye. Blepharitis is commonly classified into anterior or posterior blepharitis, with anterior affecting the lash bearing region of the lids, and posterior primarily affecting the meibomian gland orifices.

Meibomian gland disease most often occurs as one of three forms: primary meibomitis, secondary meibomitis, and meibomian seborrhea. Meibomian seborrhea is characterized by excessive meibomian secretion in the absence of inflammation (hypersecretory meibomian gland disease). Primary meibomitis, by contrast, is distinguished by stagnant and inspissated meibomian secretions (obstructive hypersecretory meibomian gland disease). Secondary meibomitis represents a localized inflammatory response in which the meibomian glands are secondarily inflamed in a spotty fashion from an anterior lid margin blepharitis.

Impaired corneal sensitivity often occurs after refractive surgery, such as photorefractive keratectomy, laser assisted sub-epithelium keratomileusis (LASEK), EPI-LASEK, customized transepithelial non-contact ablation, or other procedures in which the corneal nerves are severed. Impaired corneal sensitivity may also occur after viral infection, such as by HSV-1, HSV-2, and VZV viruses. Patients with impaired corneal sensitivity often complain that their eyes feel dry, even though tear production and evaporation may be normal, suggesting that "dryness" in such patients may actually be a form of corneal neuropathy that results when corneal nerves are severed by surgery or inflamed after viral infection.

Allergic conjunctivitis is an inflammation of the conjunctiva resulting from hypersensitivity to one or more allergens. It may be acute, intermittent, or chronic. It occurs seasonally, that is, at only certain time of the year, or it occurs perennially, that is, chronically throughout the year. Symptoms of seasonal and perennial allergic conjunctivitis include, in addition to inflammation of the conjunctiva, lacrimation, tearing, conjunctival vascular dilation, itching, papillary hyperplasia, chemosis, eyelid edema, and discharge from the eye. The discharge may form a crust over the eyes after a night's sleep.

Atopic keratoconjunctivitis is a chronic, severe form of allergic conjunctivitis that often leads to visual impairment. Symptoms include itching, burning, pain, redness, foreign body sensation, light sensitivity and blurry vision. There is often a discharge, especially on awakening from a night's sleep; the discharge may be stringy, ropy, and mucoid. The lower conjunctiva is often more prominently affected than the upper conjunctiva. The conjunctiva may range from pale, edematous, and featureless to having the characteristics of advanced disease, including papillary hypertrophy, subepithelial fibrosis, fornix foreshortening, trichiasis, entropion, and madarosis. In some patients the disease progresses to punctate epithelial erosions, corneal neovascularization, and other features of keratopathy which may impair vision. There is typically goblet cell proliferation in the conjunctiva, epithelial pseudotubular formation, and an increased number of degranulating eosinophils and mast cells in the epithelium. CD25+ T lymphocytes, macrophages, and dendritic cells (HLA-DR$^+$, HLA-CD1+) are significantly elevated in the substantia propria.

Like atopic keratoconjunctivitis, vernal keratoconjunctivitis is a severe form of allergic conjunctivitis, but it tends to affect the upper conjunctiva more prominently than the lower. It occurs in two forms. In the palpebral form, square, hard, flattened, closely packed papillae are present; in the bulbar (limbal) form, the circumcorneal conjunctiva becomes hypertrophied and grayish. Both forms are often accompanied by a mucoid discharge. Corneal epithelium loss may occur, accompanied by pain and photophobia, as may central corneal plaques and Trantas' dots.

Uveitis, the inflammation of the uvea, is responsible for about 10% of the visual impairment in the United States. Phacoanaphylactic endophthalmitis is a human autoimmune disease. Panuveitis refers to inflammation of the entire uveal (vascular) layer of the eye. Posterior uveitis generally refers to chorioretinitis, and anterior uveitis refers to iridocyclitis. The inflammatory products (i.e. cells, fibrins, excess proteins) of these inflammations are commonly found in the fluid spaces if the eye, i.e. anterior chamber, posterior chamber and vitreous space as well as infiltrating the tissue intimately involved in the inflammatory response. Uveitis may occur following surgical or traumatic injury to the eye; as a component of an autoimmune disorder, such as rheumatoid arthritis, Behcet's disease, ankylosing spondylitis, and sarcoidosis; as an isolated immune mediated ocular disorder, such as pars planitis, iridocyclitis etc., unassociated with known etiologies; and following certain systemic diseases which cause antibody-antigen complexes to be deposited in the uveal tissues. Together these disorders represent the non-infectious uveitis.

Phacoanaphylaxis is a severe form of uveitis in which the lens in the causative antigen. The lens proteins are normally secluded by the lens capsule since before birth. When these proteins are released into the eye by injury or by surgery or occasionally during cataract development, they can become intensely antigenic and incite an autoimmune response. If the response is moderate it is seen as chronic uveitis. If it is very fast in progression the eye becomes seriously inflamed in all segments. This latter response is named phacoanaphylaxis.

Uveitis is a prominent feature of Behcet's disease, a multi-system inflammatory disorder also characterized by oral and genital ulcers, cutaneous, vascular, joint, and neurological manifestations.

Rosacea is a chronic and common skin disorder with no identified cause or cure. The pathogenesis of rosacea is thought to have multiple factors. Possible factors include exposure to the demodex folliculorum mite, gastrointestinal disease or a vasodilation disorder, and other triggers such as diet or sunlight. Patients may present with a variety of symptoms, including inflammatory papules, edema, telangiectasia, rhinophyma and ocular symptoms. The ocular signs of rosacea include hyperemia, conjunctival hyperemia, ciliary base injection, bulbar injection, crusts, sleeves, and superficial punctuate keratopathy. The ocular symptoms are nonspecific and may include burning, tearing, decreased tear secretion, redness, and foreign body or gritty or dry sensation, irritation, Itchiness, Blurred vision, Photosensitivity, Watery eyes, bloodshot eyes, Burning, telangiectasia, irregularity of the lid margins, and meibomian gland dysfunction.

Pinguecula is a benign, yellowish brown proliferative growth that forms on the conjunctiva. Pinguecula may cause irritation and scratchiness of the eye, dry eye, inflammation of the conjunctiva and effect appearance of the eye. Inflamed pinguecula, which cause ocular irritation or become unsightly, may require surgical removal. However, the post-operation scar may be as cosmetically objectionable as the pinguecula and pinguecula regrowth may occur following surgical removal.

Allogeneic bone marrow transplantation (BMT) is a well-established treatment for malignant and non-malignant hematological diseases, and is performed in tens of thousands of patients each year. Mature donor T cells within the stem cell graft are the main mediators of the beneficial immune effects, but they are also responsible for the induction of graft-versus-host disease (GVHD), the major cause of morbidity and mortality in BMT patients. GVHD occurs when transplanted donor-derived T cells recognize proteins expressed by recipient antigen-presenting cells. Consequently, this recognition induces donor T-cell activation, proliferation, and differentiation, leading to a cellular and inflammatory attack on recipient target tissues. Acute or chronic GVHD occurs within a 100-day period post-BMT that leads to dermatitis, enteritis, and hepatitis. Ocular symptoms include blurry vision, foreign body sensation, burning sensation, severe light sensitivity, chronic conjunctivitis, dry eye, and eye pain.

Pharmaceutical Compositions

The present invention also relates to pharmaceutical compositions comprising at least one compound of general formula (I), the compound being present alone or in combination with one or more pharmaceutically acceptable excipients. A "pharmaceutically acceptable excipient" is one that is compatible with the active ingredient of the composition and not harmful to the person being administered the pharmaceutical composition. Mixtures of two or more of such suitable excipients may be used.

For topical ocular applications, pharmaceutical compositions may be prepared by combining a therapeutically effective amount of a compound of the invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations. The actual dose of the active compounds of the present invention depends on the specific compound, and on the condition to be treated; the selection of the appropriate dose is well within the knowledge of one of ordinary skill in the art.

U.S. Pat. No. 5,474,979, the entire contents of which are incorporated herein by reference, provides examples of ophthalmically acceptable pharmaceutical excipients. The patent discloses the vehicle used in Restasis®, cyclosporin A 0.05%, manufactured by Allergan, Inc.

What is claimed is:

1. A method of treating a condition in a mammal, the method comprising administering to the mammal in need of the treatment a compound selected from the group consisting of:

[(R)-(3-morpholin-4-yl-propylthio)-Sar]$^3$ cyclosporin A;
[(R)-(3-ethylisopropylamino-propylthio)-Sar]$^3$ cyclosporin A;
[(R)-(3-(4-methyl-piperazin-1-yl)-propylthio)-Sar]$^3$ cyclosporin A;

and pharmaceutically acceptable salts thereof;
wherein the condition is selected from the group consisting of dry eye, blepharitis, meibomian gland disease, allergic conjunctivitis, pterygium, ocular symptoms of graft versus host disease, ocular allergy, atopic keratoconjunctivitis, vernal keratoconjunctivitis, uveitis, anterior uveitis, Behcet's disease, Steven Johnson syndrome, ocular cicatricial pemphigoid, chronic ocular surface inflammation caused by viral infection, herpes simplex keratitis, ocular rosacea and pinguecula;
thereby treating the condition in the mammal.

2. The method of claim 1, wherein the condition is dry eye.

3. The method of claim 1 or 2, wherein the mammal is a human.

4. A method of restoring corneal sensitivity that has been impaired due to surgery on the cornea of an eye of a mammal, the method comprising administering to the mammal in need of the restorative treatment a compound selected from the group consisting of:

[(R)-(3-morpholin-4-yl-propylthio)-Sarr]$^3$ cyclosporin A;
[(R)-(3-ethylisopropylamino-propylthio)-Sar]$^3$ cyclosporin A;
[(R)-(3-(4-methyl-piperazin-1-yl)-propylthio)-Sar]$^3$ cyclosporin A;
and pharmaceutically acceptable salts thereof;

thereby restoring the corneal sensitivity in the mammal.

5. The method of claim 4, wherein the mammal is a human.

* * * * *